United States Patent
Woo et al.

(10) Patent No.: US 6,838,099 B2
(45) Date of Patent: Jan. 4, 2005

(54) METHOD FOR PREPARING SOLUBLE DIETARY FIBER FROM CORN HULL

(75) Inventors: Dong-Ho Woo, Incheon (KR); Jin-Keun Kim, Incheon (KR)

(73) Assignee: Samyang Genex Corporation, Seoul (KR)

(*) Notice: Subject to any disclaimer, the term of this patent is extended or adjusted under 35 U.S.C. 154(b) by 368 days.

(21) Appl. No.: 10/168,644

(22) PCT Filed: Oct. 18, 2001

(86) PCT No.: PCT/KR01/01759
§ 371 (c)(1),
(2), (4) Date: Jun. 19, 2002

(87) PCT Pub. No.: WO02/34070
PCT Pub. Date: May 2, 2002

(65) Prior Publication Data
US 2003/0003216 A1 Jan. 2, 2003

(30) Foreign Application Priority Data

Oct. 24, 2000 (KR) ........................................ 2000-62616
Oct. 15, 2001 (KR) ........................................ 2001-63445

(51) Int. Cl.$^7$ .............................. D21C 3/02; D21C 1/00
(52) U.S. Cl. .......................... 426/52; 426/626; 435/277
(58) Field of Search .......................... 426/52, 626, 627, 426/430, 436, 481, 482; 435/99, 209, 277; 127/37

(56) References Cited

U.S. PATENT DOCUMENTS 5,112,964 A * 5/1992 Aoe et al. .................... 536/56
5,622,738 A    4/1997 Takeuchi et al. ............. 426/52
6,090,595 A * 7/2000 Foody et al. ................. 435/99
6,566,125 B2 * 5/2003 Johnston et al. ............ 435/275
6,764,699 B2 * 7/2004 Rubio et al. ................. 426/52

FOREIGN PATENT DOCUMENTS

| JP | 01-242540 | 9/1989 |
| JP | 02-276801 | 11/1990 |
| JP | 03-209331 | 9/1991 |
| WO | 98/40413 | 9/1998 |

OTHER PUBLICATIONS

*Chemical Abstracts*, vol. 109, No. 2, see Abstract No. 8277 (1988).

Donner, L., et al., "Isolation of Hemicellulose from Corn Fiber by Alkaline Hydrogen Peroxide Extraction," *Cereal Chemistry*, vol. 72, No. 2, pp. 176–181 (1997).

Hromadkova, Z., et al., "Isolation and Characterization of Hemicellulose of Corn Hulls," *Chemical Papers*, vol. 49, No. 2, pp. 97–101 (1995).

* cited by examiner

*Primary Examiner*—Keith Hendricks
(74) *Attorney, Agent, or Firm*—Ladas & Parry

(57) ABSTRACT

The present invention relates to a high yield process for producing soluble dietary fiber from corn hull. More specifically, the present invention comprises removing starch and protein with enzymes from corn hull which is by-product of wet-milling process for production of corn starch, extracting the resultant with alkaline solution to form a alkaline extract, treating the alkaline extract with enzymes, and drying the enzyme-treated solution, to produce dietary fiber with low viscosity and containing hemicellulose as a major component at high yield.

8 Claims, No Drawings

METHOD FOR PREPARING SOLUBLE DIETARY FIBER FROM CORN HULL

BACKGROUND OF THE INVENTION (a) Field of the Invention

The present invention relates to a method for preparing soluble dietary fiber from corn hulls.

(b) Description of the Related Arts

In general, dietary fiber can be defined as "all the components of a plant that are resistant to digestion by human digestive enzymes."

Dietary fiber can be classified into a water-insoluble group and a water-soluble group. It has been known that soluble dietary fiber has a good effect on suppression of increase of serum cholesterol level. The mechanism of soluble dietary fiber to improve lipid metabolism is supported by the functions that soluble dietary fiber inhibits lipid absorption in the digestive tract and accelerates excretion of bile acid, and that the short chain fatty acids, in particular propionic acid produced from fermentation of the fiber in the colon, suppresses the synthesis of cholesterol. Well-known insoluble dietary fibers include cellulose, lignin, and the like, and soluble dietary fibers include Guar gum, Arabic gum, pectin, hemicellulose, and the like. In addition, indigestible components that are contained in cell walls and cell contents of plants such as grains have been called crude fiber, and they include hulls of grains such as rice, corn, and beans.

Corn hulls, produced from wet milling in the preparation process of starch, can be used as a good source of dietary fiber, because the corn hulls contain a lot of dietary fiber, and in particular more hemicellulose than hulls of other grains. Hemicellulose is a polysaccharide that consists of complicatedly connected monomers, and that is a component of cell walls of plants except for cellulose and pectin. Hemicelluloses are divided into two groups: water-insoluble hemicellulose A, and water-soluble hemicellulose B. Soluble hemicellulose B includes a main component of arabinoxylan which consists of xylose and arabinose. Arabinoxylan has a beta-1,4-linkage that cannot be hydrolyzed by human digestive enzymes, and thus can be a good dietary fiber.

There are many suggestions on preparation methods for dietary fiber from grain hulls.

Japanese Laid-Open Patent Publication Pyung 1-242540 described a process for preparing dietary fiber powder. Corn hulls were treated with glucoamylase for 24 to 40 hours to remove starch, extracted at room temperature for 18 hours after adding 0.5N NaOH solution (2%), and centrifuged. The extract was then treated with trichloroacetic acid and centrifuged again to precipitate protein.

The resultant solution was contained in a cellophane tube for dialysis in water for 3 days, and was then left after adding ethanol to obtain precipitates, which were subsequently recovered (final yield=13%).

Japanese Laid-Open Patent Publication Pyung 3-209331 disclosed a preparation method of dietary fiber powder. Corn hulls obtained from wet milling in a preparation process of corn starch were mixed in a homogenizer with the addition of water, and then filtered with a sieve. The resultant was extracted with a NaOH or $Ca(OH)_2$ solution, centrifuged, and neutralized to pH 7. The neutralized solution was dried in a drum dryer, or it was treated with alkaline xylase, purified in several processes, and then dried in a spray dryer to produce powder.

Japanese Patent Publication Pyung 6-11764 disclosed a method of to preparing soluble hemicellulose. Defatted rice bran was treated with heat-resistant amylase in hot water to remove starch, and was then extracted under an alkaline condition of pH 10 or more, or an acidic condition of pH 3 or more, to produce a solution containing a soluble hemicellulose B fraction. Insoluble components were removed by neutralizing the resultant solution and performing ultra-filtration. The resultant was purified to produce soluble hemicellulose (final yield=3.5~8%).

WO 98-40413 disclosed a preparing method for corn fiber gum with an improved color and low viscosity. Specifically, the corn hulls were destarched with heat-resistant amylase, extracted with a hydrogen peroxide, NaOH, and a $Ca(OH)_2$ solution, and then ultra-filtrated to remove insoluble components such as a hemicellulose A fraction. The resultant solution was concentrated and dried in a spray dryer. Otherwise the solution was precipitated with alcohol after concentration.

The preparing methods for soluble dietary fiber from grain hulls as mentioned above have many disadvantages, as follows. The fine fiber is removed in the removing process of starch and protein, thereby lowering the yield of fiber. Because $Ca(OH)_2$ with low water-solubility is used in the alkaline extracting process, the content of ash is high in the final sample. Thus, many purification processes are required, and the extraction yield is decreased. In addition, due to centrifugation after alkaline extraction, the extract solution cannot be recovered maximally. Thus, the final yield of soluble fiber decreases, and the maximal recovery rate according to prior arts is only 13%. Use of organic solvent such as alcohol makes the preparation process complicated and the industrialization of the process difficult.

SUMMARY OF THE INVENTION

The object of the present invention is to provide a preparing method for soluble dietary fiber that contains hemicellulose as a main component and has high transparency and low viscosity$_T$ at a high yield, from corn hulls.

DETAILED DESCRIPTION OF THE INVENTION

The present invention provides a high yield method of preparing soluble dietary fiber with a low viscosity.

The method of the present invention comprises the steps of:

(i) removing starch and protein from corn hulls;

(ii) extracting starch- and protein-removed the corn hulls with an alkaline solution, and filtering the alkaline extract through a filter cloth;

(iii) treating the filtrate of step (ii) with cellulase and cellobiase;

(iv) treating the solution reacted with enzyme of step (iii) with an adsorbent, and then filtering it through a membrane filter; and (v) purifying the filtrate.

As desired, to further improve the transparency and filterability, step (iii) further comprises a step of treatment with xylanase. Preferably, before the to enzymatic reaction, the alkaline extract is further desalted and decolorized with an ion exchange resin.

The corn hulls used in the present invention are commercially available. As long as the corn hulls are commercially available, all corn hulls can be used without considering their quality level.

In the present invention, the generally known methods for removing starch and protein can be used. For example, in the enzymatic method, the corn hulls can be treated with a starch degrading enzyme such as amylase and glucoamylase, and protease. Treatment with the starch degrading enzyme and the protease can be done simultaneously or sequentially.

In the invention, after removal of starch and protein from corn hulls, the resultant can be filtered through a filter cloth, thereby increasing the recovery rate of corn hulls.

To extract hemicellulose, which constitutes 70% or more of corn hulls, the corn hulls are stirred with the addition of an alkaline solution at a high temperature. The alkaline solution can be NaOH, or a mixture of NaOH and $Ca(OH)_2$. When only the sodium hydroxide is used, a higher yield, a higher content of dietary fiber, and more advantages in the preparation process can be expected compared to using sodium hydroxide and calcium hydroxide together. In considering the efficient extraction of hemicellulose, it is preferable to use sodium hydroxide at a low concentration. The maximal recovery rate of the extract can be reached by filtering the extract with a filter cloth after alkaline extraction.

After neutralizing the extract with acid, the resultant solution is simultaneously treated with cellulase and cellobiase, or cellulase, cellobiase and xylanase. The addition of cellulase, cellobiase, and xylanase makes the extract less viscous, more transparent, and more filterable, thereby making the production process more advantageous.

In addition, when the alkaline extract is treated by desalting and decolorization with a cation or anion exchange resin before the enzyme treatment, it is possible to reduce the amount of the enzyme which is required in the following step to produce the same quality of soluble dietary fiber.

The solution obtained from the enzyme reaction is treated with an adsorbent such as activated carbon, filtered by membrane filtration, treated with an ion exchange resin, concentrated, and dried, to produce the water-soluble dietary fiber.

The preparing method of the soluble dietary fiber from corn hulls is more specifically described in the following.

First Step: Removal of Starch and Protein from Corn Hulls

Corn hulls obtained from corn starch production are dried to about 5% of water content. The dried corn hulls are mixed with distilled water in the amount of 10 to 20 times, preferably 15 times by weight of the corn hulls, and the pH is adjusted to pH 5.8 to 6.0 by the addition of a 3 to 5% NaOH standard solution. After the resultant solution is heated by stirring in a water bath so that the temperature of the solution is 90 to 100° C., the solution is stirred for 1 to 5 hours with the addition of alpha-amylase in the amount of 0.05 to 5%, preferably 0.1 to 3% to the dried corn hulls, and then filtered through a filter cloth, and the corn hulls are then sufficiently washed with water. The alpha-amylase, for example Termamyl (Novo Nordisk LTD.), is preferably heat-resistant. The filter cloth can be a generally used one that is made from polyester and polyamide with an internal pore size of 36 to 100, and preferably 44 to 53 micrometers.

Destarched corn hulls are then suspended in distilled water in the same ratio as above, and the pH of the solution is adjusted to pH 7.0 by the addition of a sodium hydroxide solution. After the resultant solution is heated by stirring in a water bath so that the temperature of the solution is 45 to 55° C., it is stirred for 1 to 5 hours with the addition of protease in the amount of 0.05 to 5%, preferably 0.2 to 2%, filtered through the filter cloth, and washed by the same method as above, to obtain starch- and protein-removed corn hulls. The proteases include fungi enzymes such as flavourzyme derived from *Asperfillus oryzae*, alkalase derived from *Bacillus licheniformis*, and the like. When filtration is performed with the filter cloth, the recovery rate of corn hulls is higher than with centrifugation, which is shown in Example 1.

Second Step: Alkaline Extraction

The hemicellulose is extracted from the starch- and protein-removed corn hulls with an alkaline solution. The corn hulls filtered can be used directly, or after being dried to some extent. The resultant corn hulls can be mixed with a sodium hydroxide solution at a low concentration of 0.1 to 3%, preferably 0.5 to 0.7% in the amount of 15 to 25 times, preferably 20 to 25 times by weight of the corn hulls. Then the hemicellulose is extracted by heating the mixture in a water bath, and stirring at 70 to 90° C. for 1 to 5 hours. The resultant is then cooled to room temperature, and filtered by vacuum filtration with a filter cloth to is produce the extract. The same type of filter cloth as used in the first step can be used. As shown in Example 3, when filtering with a filter cloth, the recovery rate and transparency of the alkaline extract increases, thereby improving the filterability and final yield in the following process, compared to centrifugation.

Third Step: Desalting and Decolorization

After preparing the alkaline extract, the solution can be directly treated with enzymes such as cellulose, cellobiase, and xylanase, etc. However, before the enzyme treatment, the alkaline extract can be further desalted and decolorized with an ion exchange resin. This case has advantages in that a smaller amount of enzymes is required in the enzyme reaction, and it results in a higher yield than with direct enzyme treatment without desalting and decolorization.

The ion exchange resin which is generally used for preparation of starch sweetner can be used in the desalting and decolorizing step. As examples, a strongly acidic cation exchange resin or a weakly basic anion exchange resin can be used. The ion exchange resins can be added in the amount of 1 to 10 times, and preferably 4 times the volume of the dried corn hulls. For example, a cation exchange resin including the strongly acidic styrene resin SK1B can be used, and the anion exchange resin s that can be used include a strongly basic Cl-type and a weakly basic OH-type styrene resin.

Fourth Step: Enzyme Treatment

The pH of the alkaline extract, or the desalted and decolorized alkaline extract, is adjusted to pH 4.0 to 5.5, preferably 4.7 to 5.0, which is optimum for enzymes. Then the temperature of the resultant solution is adjusted to an appropriate temperature for the active enzymes by heating it in a water bath, and it is treated with cellulase and cellobiase while stirring. Preferably, xylanase may be used for treatment together with the cellulase and cellobiase, thereby obtaining an enzyme hydrolysate with an improved filterability, low viscosity, and high transparency.

In regard to the preferred dosage content of the enzymes, when the alkaline extract is directly treated with enzymes, the dosage of cellulase and cellobiase are the same, at 0.1 to 5%, preferably 0.1 to 3%, respectively. When the amount of the enzymes is lower, it is difficult to perform the following processes, such as the filtering step. When the amount of the enzymes is higher, the reaction time is reduced, but the production costs increase.

When the alkaline extract is treated with enzymes after a desalting and decolorizing step, 10 to 90 parts by weight of cellobiase to 100 parts by weight of cellulase can produce a final product with a quality level equivalent to that of an enzyme reaction on an alkaline extract lacking the desalting and decolorizing step. The content of cellulase can be 0.1 to 5 wt % to weight of lo dried corn hulls. The cellobiase can be used in the amount of 0.1 to 5 wt %, preferably 0.1 to 3 wt %, to weight of the dried corn hulls.

Fifth Step Adsorbent Treatment and Filtration

The enzyme reaction mixture is treated with an adsorbent, and then filtered. The adsorbents include activated carbon, an adsorbing resin such as polystyrene, and the like. To obtain a transparent extract, the filtration process can be performed with a membrane filter with a pore size of 0.5 micrometer or less, and preferably 0.45 to 0.2 micrometer or less.

Sixth Step: Final Purification, Concentration and Drying

The final purification of the extract can be performed by desalting and decolorizing with an ion exchange resin which is generally used in the preparation process of dietary fiber. For example, the ion exchange resins include a strongly acidic cation exchange resin, a weakly basic anion exchange resin, and a mixed ion exchange resin. The mixed resin can be a mixture of an activated strongly acidic cation exchange resin and a strongly basic anion exchange resin, in the volume ratio of 1:2. For example, the cation exchange resins include a strongly acidic styrene resin SK1B, and the anion exchange resins include a strongly basic Cl-type styrene resin and a weakly basic OH-type styrene resin.

The finally purified enzyme hydrolysate is concentrated to a 10% solution under vacuum, and is then freeze-dried or spray-dried to produce powder. The employment of the third step in the preparation process for the dietary fiber can omit the purification process with the cation exchange resin or to anion exchange resin, resulting in simplifying the preparation process.

The following examples are intended only to illustrate the invention and are not intended to limit the scope of the invention as defined by the claims.

EXAMPLE 1

Dried corn hulls (2.8% of water content) were added to distilled water in the amount of 15 times by weight of the dried corn hulls, and the pH was adjusted to 5.8 with 1N NaOH while mixing with a mechanical stirrer. The mixture was heated in a 95° C. water bath, reacted for 2 hours with the addition of heat-resistant alpha-amylase (Novo Nordisk Ltd., Termamyl 120 LS, Denmark) in the amount of 2.0% to the dried corn hulls, filtered by a polyester filter cloth (Samsung Canvas, 55-5528, Korea), and washed with distilled water.

The destarched corn hulls were added to distilled water in the amount of 15 times by weight of the dried corn hulls, and the pH was adjusted to 7.0 with 1N NaOH while mixing with a mechanical stirrer. The mixture was reacted with the addition of protease (Novo Nordisk Ltd., Flavourzyme, Denmark) in the amount of 2.0% to the dried corn hulls for 2 hours in a 50° C. water bath, filtered by a polyester filter cloth (Samsung Canvas, 55-5528, Korea), and washed with distilled water. The resultant was dried in an oven at 50° C., to produce starch- and protein-removed corn hulls. The yield of corn hulls is shown in Table 1.

EXAMPLE 2

The same method as in Example 1 was used, except that instead of Flavourzyme, alkalase (Novo Nordisk Ltd., Alkalase, Denmark) in the amount of 2.0% to the dried corn hulls was reacted for 2 h ours in a 55° C. water bath, to produce starch- and protein-removed corn hulls. The yield of corn hulls is shown in Table 1.

COMPARATIVE EXAMPLE 1

The same method as in Example 1 was used, except that after the treatment of alpha-amylase and protease, the resultant solution was centrifuged at 3,000 rpm instead of filtering with the filter cloth, to produce starch- and protein-removed corn hulls. The yield of corn hulls is shown in Table 1.

TABLE 1

The yield of starch- and protein-removed corn hulls

| | Yield of corn hulls (%)[1] | Remark |
|---|---|---|
| Vacuum filtration (Example 1) | 73.7 | Polyester filter cloth |
| Vacuum filtration (Example 2) | 74.2 | Polyester filter cloth |
| Centrifugation | 65.0 | Vacuum filtration |

[1]yield of corn hulls = (starch- and protein-removed dried corn hulls/raw corn hulls) × 100

EXAMPLE 3

Preparation of Alkaline Extract 37 g of starch- and protein-remvoed corn hulls prepared according to Example 1 were mixed with 1 L of a 0.5% NaOH solution, and stirred in an 80° C. water bath for 3 hours, and filtered through a filter cloth to produce a primary alkaline extract. The yield and transparency as measured with a spectrophotometer are shown in Table 2

COMPARATIVE EXAMPLE 2

The corn hulls obtained in Comparative Example 1 were treated with an alkaline solution as in Example 3, and then they were centrifuged instead of filtered, to produce an alkaline extract. The yield and transparency as measured with a spectrophotometer are shown in Table 2. The results show that the yield and transparency with vacuum filtration are higher than with the centrifugation method.

TABLE 2

| | Yield (%)[1] | Transparency (%)[2] | Treatment type |
|---|---|---|---|
| Example 3 | 55.3 | 62.7 | Vacuum filtration with polyester filter cloth |
| Comparative Example 2 | 47.6 | 34.3 | Centrifugation |

[1]Yield = (solid content of alkaline extract/raw corn hulls) × 100
[2]Transparency (2%, 720 nm, distilled water was 100%)

EXAMPLE 4

Enzymatic Treatment

The pH of 1.2 L of the primary extract obtained in Example 3 (27.7 g of solid content) was adjusted to pH 4.8 by the addition of 10% HCl, and cellulase (Novo Nordisk Ltd, Celluclast, Denmark) and cellobiase (Novo Nordisk Ltd., to Novozyme 188, Denmark) were added in the amount of 3% by weight of the dried corn hulls in a 50° C. water bath. Then, the viscosity, filterability, and transparency of the resultant solution were measured, and the results are shown in Table 3. To compare the results, the above process was repeated, except that only 3.0% by weight of the cellulase was used.

In addition, the pH of the same primary extract as above was adjusted to pH 4.8 by the addition of 10% HCl, and cellulase (Novo Nordisk Ltd, Celluclast, Denmark), cellobiase (Novo Nordisk Ltd., Novozyme 188, Denmark), and xylanase (Biocatalyst Co., Depot 333p, UK) in the amount of 3% by weight of the dried corn hulls were added simultaneously to the extract, reacted in a 60° C. water bath for 3 hours. Then, the viscosity, the filterability, and the transparency of the resultant solution were measured, and the results are shown in Table 3.

2.5 g of activated carbon (Norit Co., KB-B, Holland) were added to an enzyme hydrolysate of three enzymes, it was heated to 95° C. for 30 seconds, and cooled to room temperature. The resultant was primarily filtered into filter paper (Advantec Co., Toyo 5A, Japan), and then secondly into filter paper (Whatman International Ltd., GF/B, UK) in a glass filter under vacuum. Then, the resultant was filtered through a membrane with a pore size of 0.45 micrometers (Gelman Co., Metricel, USA) and a membrane with a pore size of 0.2 micrometers (Gelman Co., Super-200, USA).

The obtained filtrate was treated with a strongly acidic cation exchange resin (Samyang Co., SK-1B, Korea), a weakly basic and strongly basic anion exchange resin (Samyang Co., WA 30; PA 408, Korea), and a resin mixture (strongly acidic cation exchange resin and strongly basic anion exchange resin in the ratio of 1:2) at each step, it was stirred in a 40° C. water bath for 1.5 hours, filtered, and desalted and decolorized.

Finally, the resultant was concentrated with a vacuum evaporator (EYELA, NE-1V, Japan), so that the concentration of the soluble dietary fiber was measured to be 10% (w/w). The final yield of soluble dietary fiber to raw corn hulls was 23.1%. As a result of measurement of the fiber with a Prosky-AOAC method, the content of soluble dietary fiber was 91.9%, and the results of typical analysis are shown in Table 4.

TABLE 3

Viscosity, Filterability, and Transparency of enzyme hydrolysate[1] depending on the condition of the enzyme treatment

| Condition of enzyme treatment | Viscosity[2] (cps) | Filtering rated[3] (second) | Transparency[4] (%) |
|---|---|---|---|
| Cellulase | 15.0 | Not filtered | 6.4 |
| Cellulase + cellobiase | 10.0 | 201 | 64.7 |
| Cellulase + cellobiase + xylanase | 8.0 | 55 | 95.5 |

[1]After the enzyme reaction, the solution was filtered with filter paper (Watman Filter Paper, GF/B)
[2]Viscosity was measured with a viscometer (Spindle No. 2, 60 rpm, room temperature)
[3]The time required for 30 mL of enzyme hydrolysate to filter through filter paper (GF/B)
[4]The transparency was measured with a spectrophotometer (5% concentration, 720 nm, the distilled water was 100%)

TABLE 4

Analysis of components, pH, viscosity and transparency of soluble dietary fiber prepared from corn hulls

| Item | Result | Analytical method |
|---|---|---|
| Water (%) | 5 or less | Oven drying method |
| Crude protein (%) | 0.7 | Kjeldahl method |
| Crude lipid (%) | 0.1 | Soxhlet method |
| Crude ash (%) | 0.4 or less | Incineration method |
| pH (at 5% concentration) | 3.0~5.0 | pH meter |
| Viscosity (cps, at 5% concentration) | 8~12 | Viscometer (LVF type) |
| Transparency (T %, at 5% concentration) | 95 or more | Spectrophotometer |

EXAMPLE 5

Desalting and Decolorizing Process

To perform the desalting and decolorizing process, the pH of 1.2 L of primary extract obtained in Example 3 (27.7 g of solid content) was adjusted to pH 6.0 by adding 10% HCl, and 200 mL of the strongly acidic cation exchange resin (Samyang Co., SK-1B, Korea) and the weakly basic anion exchange resin (Samyang Co., WA 30, Korea) were added sequentially, it was stirred in a 40° C. water bath for 1.5 hours, and then filtered.

The pH of the resultant solution was adjusted to pH 4.8, cellulase (Novo Nordisk Ltd, Celluclast, Denmark) and cellobiase (Novo Nordisk Ltd., Novozyme 188, Denmark) were added in the amount of 2% and 0.4% by weight of the dried corn hulls respectively, and it was reacted for 3 hours in a 50° C. water bath. Then, the viscosity, the filterability, and the transparency of the resultant solution were measured, and the results are shown in Table 5. To compare the results, the above process was repeated, except that only 2.0% of the cellulase was used.

In addition, the pH of the same primary extract as above was adjusted to pH 6.0, and then it was desalted and decolorized according to the method as mentioned above. Then, the pH of the resultant solution was adjusted to 4.8, cellulase (Novo Nordisk Ltd, Celluclast, Denmark), cellobiase (Novo Nordisk Ltd., Novozyme 188, Denmark), and xylanase (Biocatalyst Co., Depol 333p, UK) were added simultaneously in the amount of 2.0%, 0.4%, and 2.0% by weight of the dried corn hulls respectively, and it was reacted in a 55° C. water bath for 3 hours. Then, the viscosity, the filterability, and the transparency of the resultant solution were measured, and the results are shown in Table 5.

2.5 g of the activated carbon (Norit Co., KB-B, Holland) were added to an hydrolysate of three enzymes, it was heated to 95° C. for 30 seconds, and cooled to room temperature. The resultant was primarily filtered into filter paper (Advantec Co., Toyo 5A, Japan), and then secondly into filter paper (Whatman International Ltd., GF/B, UK) in a glass filter under vacuum. Then, the resultant was filtered into a membrane with a pore size of 0.45 micrometers (Gelman Co., Metricel, USA) and a membrane with a pore size of 0.2 micrometers (Gelman Co., Super-200, USA).

The obtained filtrate was added to 200 mL of a resin mixture of a strongly acidic cation exchange resin (Samyang Co., SK-1B, Korea) and a weakly basic anion exchange resin (Samyang Co., WA 30; PA 408, Korea) in the volume ratio of 1:2, and stirred in a 40° C. water bath for 1.5 hours to complete the final purification process.

Finally, the resultant solution was concentrated with a vacuum evaporator (EYELA, NE-1V, Japan), so that the concentration of the soluble dietary fiber was measured be to 10% (w/w). The final yield of soluble dietary fiber to raw corn hulls was 24.5%. As a result of measurement of the fiber with a Prosky-AOAC method, the content of soluble dietary fiber was 92.1%, and the results of typical analysis are shown in Table 6.

TABLE 5

Viscosity, Filterability, and Transparency of enzyme hydrolysate[1] depending on the condition of the enzyme treatment

| Condition of enzyme treatment | Viscosity[2] (cps) | Filtering rated[3] (second) | Transparency[4] (%) |
|---|---|---|---|
| Cellulase | 15.0 | Not filtered | 6.4 |
| Cellulase + cellobiase | 9.5 | 190 | 68.0 |

TABLE 5-continued

Viscosity, Filterability, and Transparency of enzyme hydrolysate[1]
depending on the condition of the enzyme treatment

| Condition of enzyme treatment | Viscosity[2] (cps) | Filtering rated[3] (second) | Transparency[4] (%) |
|---|---|---|---|
| Cellulase + cellobiase + xylanase | 9.0 | 57 | 96.1 |

[1]After the enzyme reaction, the solution was filtered with filter paper (Watman Filter Paper, GF/B)
[2]Viscosity was measured with a viscometer (Spindle No. 2, 60 rpm, room temperature)
[3]The time required for 30 mL of enzyme reaction solution to filter through filter paper (GF/B)
[4]The transparency was measured with a spectrophotometer (5% concentration, 720 nm, the distilled water was 100%)

TABLE 6

Analysis of components, pH, viscosity, and transparency of soluble dietary fiber prepared from corn hulls

| Item | Result | Analytical method |
|---|---|---|
| Water (%) | 5 or less | Oven drying method |
| Crude protein (%) | 0.6 | Kjeldahl method |
| Crude lipid (%) | 0.1 | Soxhlet method |
| Crude ash (%) | 0.5 or less | Incineration method |
| pH (at 5% concentration) | 3.0~5.0 | PH meter |
| Viscosity (cps, at 5% concentration) | 8~12 | Viscometer (LVF type) |
| Transparency (T %, at 5% concentration) | 95 or more | Spectrophotometer |

EXAMPLE 6

This example was produced according to the same method of Example 4, except that xylanase derived from Aspergillus niger (Novo Nordisk Ltd., Shearzyme 500 L, Denmark) was used instead of xylanse. The final yield of dietary fiber to raw corn hulls was 20.4%, and the content of dietary fiber was 90.7%.

EXAMPLE 7

200 g of corn hulls (5.7% of water content) were mixed with distilled water so that the final concentration was 8%, 1N NaOH solution was added while mixing with an a mechanical stirrer, to a pH of 5.8. The mixture was heated in a 95° C. water bath, reacted with the addition of the heat-resistant alpha-amylase of Example 1 in the amount of 1.0% (v/w) to the dried corn hulls, for 2 hours, and filtered with a filter cloth. The destarched corn hulls were added to 3.0 L of distilled water, and the pH was adjusted to 7.0 with 1N NaOH solution. The mixture was reacted with protease (Novo Nordisk Ltd., Flavourzyme, Denmark) in the amount of 1.0 (w/w) % to the dried corn hulls for 3 hours in a 50° C. water bath, filtered with a filter cloth, and dried in an oven at 50° C., to produce starch- and protein-removed corn hulls. The yield of corn hulls was 74.0%. To perform alkaline extraction, the starch- and protein-removed corn hulls were mixed with 3 L of a 0.5% NaOH solution, and stirred in a 40° C. water bath for 24 hours and filtered through a filter cloth to produce a primary alkaline extract. The pH of the primary extract was adjusted to pH 4.8 by addition of 10% of HCl, and cellulase (Novo Nordisk Ltd, Celluclast, Denmark) and cellobiase (Novo Nordisk Ltd., Novozyme 188, Denmark) in the amount of 1.0% by weight of the dried corn hulls were respectively added, and reacted in a 50° C. water bath for 5 hours. After the reaction, 10% (w/w) of the activated carbon (Norit Co., KB-B, Holland) to corn hulls was added to the hydrolysate of three enzymes, it was heated to 95° C. for 30 seconds, and cooled to room temperature. The resultant was finally filtered with a membrane with a pore size of 0.45 micrometers (Gelman Co., Metricel, USA). As in the method of Example 3, the desalting and decolorizing steps were performed with three steps of ion exchange resin treatment. The resultant solution was concentrated so that the final concentration was 10% (w/w), and then the final yield of soluble dietary fiber to the raw dried corn hulls was calculated. As a result, the yield was 21.5%, and the content of the fiber was 86.4%.

EXAMPLE 8

According to the method of Example 1, 300 g of corn hulls were added to distilled water in the amount of 15 times by weight of the corn hulls, and then starch and protein were removed with enzyme sequentially. The yield of starch- and protein-removed corn hulls was 68.6%.

Alkaline extraction was performed on the corn hulls with 5 L of 0.5% NaOH, and then the resultant solution was divided into two groups. 5% of Cellulase and 5% (v/w) of cellobiase to the dried corn hulls were added to one group, and reacted at 50° C. for 5 hours. 5% (v/w) of Cellulase, 5% (v/w) of cellobiase, and 5% (v/w) of xylanase to the dried corn hulls were added simultaneously to the other group and reacted at 60° C. for 5 hours. The two groups were treated according to the purification process as above. Then, the concentrations of dietary fiber solution were adjusted to 5% (w/w) at room temperature, and the viscosities were measured. As a result, with the treatment of cellulase and cellobiase, the viscosity was 10.0 cps. With the treatment of cellulase, cellobiase, and xylanase, the viscosity was 9.0 cps. For reference, Arabic gum (MSC Co., No. 10308, Korea), which is usually used as an emulsion stabilizer for food, had a viscosity of 6.7 cps.

EXAMPLE 9

After the starch and protein were removed from the corn hulls according to the method of Example 1, the resultant was divided into two groups. One group was treated with 0.5% of an alkaline mixture which included NaOH and $Ca(OH)_2$ in the same ratio in the amount of 20 times by weight of corn hulls. The other group was treated with 0.5% of a NaOH solution in the same amount, and reacted at 80° C. for 3 hours. As disclosed in Example 4, the resultant solutions were treated with the three kinds of enzymes in the amount of 3% respectively, reacted, purified, and the yield was calculated. As a result, in the case of treatment with NaOH and $Ca(OH)_2$, the yield was 15.1%, and the content of dietary fiber was 72.7%. In the case of treatment with NaOH, the yield was 20.1%, and the content of dietary fiber was 84.3%.

EXAMPLE 10

After the starch and protein were removed from the corn hulls according to the method of Example 1, the resultant was divided into three groups. The groups were treated with a 0.1%, 0.5%, and 1.0% NaOH solution in the amount of 20 times by weight of corn hulls, respectively. As disclosed in Example 4, the resultant solutions were treated with the three kinds of enzymes in the amount of 3% respectively, reacted, purified, and the yield was calculated. As a result, when treating with 0.1%, 0.5%, and 1.0% NaOH, the yields were 3.3%, 30.0%, and 33.4%, respectively. However, the treatment with 1.0% NaOH caused the formation of salt in

EXAMPLE 11

After the starch and protein were removed from the corn hulls according to the method of Example 1, the resultant was divided into three groups. The groups were treated with a 0.5% NaOH solution in the amount of 20 times by weight of corn hulls for 1, 3, and 10 hours, respectively. As disclosed in Example 4, the resultant solutions were treated with the three kinds of enzymes in the amount of 3% respectively, reacted, purified, and the yield was calculated. As a result, when treatment time was 1, 3, and 10 hours, the yields were 24.9%, 27.9%, and 26.7%, respectively.

EXAMPLE 12

After the starch and protein were removed from the corn hulls according to the method of Example 1, the resultant was divided into three groups. The groups were treated with a 0.5% NaOH solution in the amount of 20 times by weight of corn hulls for 3 hours at 40, 60, and 80° C., respectively. As disclosed in Example 4, the resultant solutions were treated with the three kinds of enzymes in the amount of 3% respectively, reacted, purified, and the yield was calculated. As a result, when treatment temperature was 40, 60, and 80° C., the yields were 8.5%, 15.4%, and 21.7%, respectively.

EXAMPLE 13
Emulsion Stability Test

Lecithin powder (Central Soya Co., Centrolex D, USA), Arabic gum (MSC Co., 10308, Korea), and two kinds of dietary fiber extracted from corn hulls at 2% (w/w) respectively were added to a mixture of soy bean oil and distilled water, emulsified with a homogenizer at 20,000 rpm for 5 minutes, and the viscosity of the emulsion was measured. As a result, the viscosity was 23 cps for lecithin powder, 35 cps for Arabic gum, 55 cps for dietary fiber obtained by treating with cellulase and cellobiase, and 50 cps for dietary fiber obtained by treating with cellulase, cellobiase, and xylanse.

In addition, the state of emulsion in a 100 mL mass cylinder was investigated. As a result, all the samples showed good emulsion stability. After 10 days, a lower aqueous layer separation occurred for all the samples. After 30 days, a lower aqueous layer completely separated from the upper oil layer for the sample including lecithin, but the emulsion of the samples including Arabic gum and dietary fiber extracted from corn hulls kept comparatively stable.

What is claimed is:

1. A method of preparing a soluble dietary fiber comprising the steps of:
   (i) removing starch and protein from corn hulls;
   (ii) extracting the starch- and protein-removed corn hulls with an alkaline solution, and filtering the alkaline extract through filter cloth;
   (iii) treating the filtrate of step (ii) with cellulase and cellobiase;
   (iv) treating the solution of step (iii) with adsorbent, and filtering it through a membrane filter; and
   (v) purifying the filtrate.

2. The method of claim 1, wherein in the step (i), the corn hulls are treated with amylase and protease simultaneously or sequentially.

3. The method of claim 2, wherein in the step (i), after the treatment of amylase or protease, the resultant is filtered through a filter cloth.

4. The method of claim 1, wherein in the step (ii), the alkaline solution is a 0.1 to 0.3% of NaOH solution.

5. The method of claim 1, wherein the step (iii) further comprises a step of treating with xylanase.

6. The method of claim 1, wherein the cellulase and cellobiase are 0.1 to 5% to the dried corn hulls, respectively.

7. The method of claim 1, wherein before the step (iii), the alkaline extract from step (ii) is neutralized, and it is desalted and decolorized with an ion exchange resin.

8. The method of claim 7, wherein the cellulase and cellobiase are 0.1 to 3% to the dried corn hulls, respectively.

* * * * *